(12) United States Patent
Konovalov et al.

(10) Patent No.: US 8,735,316 B2
(45) Date of Patent: May 27, 2014

(54) CATALYST FOR AKILI-FREE PURIFICATION OF OIL RAW MATERIALS FROM MERCAPTANS

(71) Applicants: Vladmir Konovalov, Moscow Region (RU); Irina Tarkhanova, Moscow (RU); Sergey Chernyshev, Moscow Region (RU)

(72) Inventors: Vladmir Konovalov, Moscow Region (RU); Irina Tarkhanova, Moscow (RU); Sergey Chernyshev, Moscow Region (RU)

(73) Assignee: Greendane Limited, Nicosia (CY)

( * ) Notice: Subject to any disclaimer, the term of this patent is extended or adjusted under 35 U.S.C. 154(b) by 61 days.

(21) Appl. No.: 13/653,902

(22) Filed: Nov. 17, 2012

(65) Prior Publication Data

US 2013/0137888 A1    May 30, 2013

Related U.S. Application Data

(62) Division of application No. 12/800,864, filed on May 24, 2010, now Pat. No. 8,524,072.

(51) Int. Cl.
*B01J 31/16* (2006.01)
*B01J 31/30* (2006.01)

(52) U.S. Cl.
USPC ............ 502/171; 502/169; 502/172; 556/113

(58) Field of Classification Search
USPC .......................... 502/169, 171, 172; 556/113
See application file for complete search history.

(56) References Cited

U.S. PATENT DOCUMENTS 3,378,484 A * 4/1968 Ferrara et al. .................. 502/11

* cited by examiner

*Primary Examiner* — Randy Boyer
(74) *Attorney, Agent, or Firm* — Henry M. Feiereisen, LL

(57) ABSTRACT

A catalyst for alkali-free purification of oil raw materials includes a solid metalocomplex or a liquid metalocomplex with a general formula $(Cu^MCl)20(Li)2^{\hat{}}(L_2)i^{\hat{}}$, where Li is amino alcohol, L2 is acetonitryl or single atom alcohol.

3 Claims, No Drawings

CATALYST FOR AKILI-FREE PURIFICATION OF OIL RAW MATERIALS FROM MERCAPTANS

CROSS REFERENCE TO A RELATED APPLICATION

The present application is a division of U.S. patent application Ser. No. 12/800,864, filed on May 24, 2010.

The present application contains a subject matter which is similar to a part of the subject matter of the above identified earlier patent application, from which it claims its priority under 35 USC 119 (a)-(d), and which is incorporated in the present application by reference thereto.

BACKGROUND OF THE INVENTION

The present invention relates to catalysts for purification of gaseous condensate and oil fractions from mercaptans and can be used in oil-processing and in petrochemical industry.

Usually oxidation of mercaptans is performed by oxygen or air at room or elevated temperature in the presence of homogenous or heterogeneous catalyst based on a transitional metal:

$$2RSH + \tfrac{1}{2}O_2 \rightarrow RSSR + H_2O$$

Mercaptans are extracted from organic phase by strongly alkali aqueous solutions, in which at elevated temperature and pressure catalytical oxidation of mercaptans takes place, and as a catalyst salts from metals of alternating valency (Fe, Co, Ni, V, Mn, Cr) in the form of simple or complex compositions, more often phatocyanites (as disclosed for example in European patent no. 394571, German patent 3008284 and others). The catalysts of this type provide sufficiently complete removal of mercaptans. Their common disadvantage is not sufficient availability and high cost of phatocyanites, which leads to making the process of purification expensive. Moreover, the necessity to conduct the process in strongly-alkli medium leads to a significant corrosion of equipment and worsening of the properties of oil pipelines.

It is known that phtalocyanines in catalytical compositions can be replaced with other compounds of transitional metals.

A catalyst are known based on metallo-organic derivatives of metals of VIA, VIIA, and VIII groups with general formula $Me_a(R)x(CO)y$ where R is aromatic ligand, for example benzol or its alkyl derivatives, antrazen, benzpirin, phenanthren (U.S. Pat. No. 3,053,756). Disadvantages of such catalysts include their low stability, high cost and toxicity.

A catalyst for oxidating demercaptanization of carbohydrates is known which is a helate complex of a transitional metal with bi, tri, or tetra dentant ligand, containing at least one amide group (French patent 2,573,087). In particular, replaced 2-(alkyl(aryl, aklylary))-aminocarboxypyriditines and others even more complicated compounds are utilized. As a metal it can be Co, Fe, Cu, Ni, Mn. The disadvantage is a low stability of the catalyst and use for its manufacture of expensive and scarse components.

Also, catalysts of oxidating demercaptanization are known-complexes of copper with tetracyantiophenol and tetracyandentin (French patent 2591610). These catalysts provide high degree of purification, but their practical use is questionable because their very high cost and scarse availability of the components.

A method of oxidative demercaptinization are known which is performed by oxidation of mercaptans with oxygen of air in presence of helate complexes of a transitional metal (Co, Fe, Cu, Ni, Mn) with polydentan ligand from the class of amides, in particular from aminocarboxyperidines (French patent 2573087). The main disadvantage of the method with the use of this catalyst is high cost of its components.

A heterogeneous catalyst is described, based on complexes of copper with amino derivatives (aminoalcohols, aminoacids, amines) applied on a mineral carrier or activated coal (European patent 996500). The disadvantage of this catalyst is a low content of active phase on the surface of the carrier, which inevitably leads to a significant consumption of the heterogeneous catalyst.

The closest solution to the present invention is disclosed in U.S. Pat. No. 7,087,547. In accordance with this patent, a catalyst of alkali-free purification of oil fractions from mercatans is proposed, which contains a copper oxide, a complex of copper with nitrogen-containing compound of amines, aminoalcohols, aminoacids, or amids and an inert carrier. The disadvantage of this method is a complex technology for producing catalyst and a high consumption of the carrier, which makes the catalyst quite expensive.

SUMMARY OF THE INVENTION

The objective of this invention is to reduce the cost of a catalytic composition by eliminating utilization of a mineral carrier and using solid or liquid complexes which contain a copper chloride, aminoalcohol and acetonitryl or single-atom alcohol selected from isopraponal, butanol, isobutanol, and pentanol.

In accordance with the invention a catalyst is proposed for alkali-free purification of oil raw materials, consisting of a metalocomplex selected from the group consisting of a solid metalocomplex and a liquid metalocomplex with a general formula $(Cu^{II}Cl)_2O(L_1)_{2-4}(L_2)_{1-4}$, where $L_1$ is amino alcohol, $L_2$ is acetonitryl or single atom alcohol.

in accordance with a further feature of the invention as the aminoalcohol a compound of a general formula $N(R_1)(R_2)(R_3)(OH)_{1-3}$ is utilized, where $R_1=C_2H_4$, $R_2=H$, $C_2=H$, $C_2H_4$, $C_2H_5$, $R_3=H$, $C_2H_4$, $C_nH_{2n+1}$, where n=2-17.

In accordance with still a further feature of the invention as a single atom alcohol a substance selected from the group consisting of isopropanol, butanol, isobutanol and pentanol is utilized.

The novel features which are considered as characteristic for the present invention are set forth in particular in the appended claims.

The invention itself, however, both as to its composition and its method of use, will best best understood from the following description of the preferred embodiments, which is accompanied by examples of realization.

DESCRIPTION OF THE PREFERRED EMBODIMENTS

The present invention resides, in a catalyst for purification of oil raw material with the use of a metalocomplex of general formula $(Cu^{II}Cl)_2O(L_1)_{2-4}(L_2)_{1-4}$, wherein $L_1$ is amino alcohol of the general formula $N(R_1)(R_2)(R_3)(OH)_{1-3}$, wherein $R_1=C_2H_4$, $R_2=H$, $C_2H_4$, $C_2H_5$, $C_2H_5$, $R_3=H$, $C_2H_4$, $C_nH_{2n+1}$, wherein n=2-17, $L_2$ is acetonitryl or the above mentioned alcohol.

The metal complex is synthesized in acetonitryl or alcohol starting from CuCl and aminalcohol at 45-50° C. in air.

The catalyst actively oxidizes mercaptans and hydrogen sulfide with oxygen of air at temperature 22-120° C. and at atmospheric pressure.

The objective of the present invention can not be achieved if at least one of the above mentioned components of catalytic complex are not used or the conditions of synthesis are not complied with, for example:

If instead of copper chloride CuCl2 is used or another salt is used (nitrate, sulfate, stearate, etc.)

If amino alcohol is not used, the complex is not active;

If as a solvent acetylnitryl or alcohol is not used, the activity of catalyst is reduced. For example, if acetylnitryl is replaced with chloroform, the activity of catalyst is reduced three times.

Therefore, the present invention resides in a catalyst of oxidating alkali-free demercaptanization of oil, gas condensate or oil fraction based on a metalocomplex of the above mentioned composition.

The present invention is illustrated by the following examples.

Example 1

Producing of Solid Metalocomplex 100 ml of saturated solution of CuCl in acetonitryl (the solution contains 8 g of CuCl) is introduced into a flat-bottom container of 200 ml at room temperature, and heated to 45-50° C. With continuous steering by a magnetic stirrer, slowly (in 30-40 min) from a peeped 20 ml of solution of monoethanolamine in acetonenitryl is introduced into the container (solution is prepared by mixing of 17 ml of monoethanolamine and 100 ml of acetonitryl).

The precipitated substance of blue-green color is separated from a mother solution on a filter, dried on air and then in a drying cabinet at 100-105° C. The obtained dry complex contains 9.2-9.5 g. Before testing the solid catalyst is comminuted in a porcelain dish. This way, catalyst A is produced. Catalyst B and C were produced analogously, but instead of monoethanolamine, dimethylamineethanol ethanol and three ethanolamine were utilized Example 2

Production of Liquid Metalocomplex D-F 20 ml of aminoalcohol Atmer 163 which is a mixture of isomers with the composition $RN(CH_2CH_2OH)_2$, where $R=C_nH_{2n+1}$ n=16-17 and 20 ml isobutanol is introduced into a flat bottom container. During mixing and heating to 45-50° C. in air, slowly log CuCl is added. As a result, a dark-brown dense liquid is produced. Before testing, the obtained liquid complex D is dissolved in an excessive quantity of isobutanol to concentration Cu(II) 1-1.5%. Catalyst E and F are produced analogously, but instead of isobutanol, butanol and isopropanol were added.

Example 3

Production of Liquid Metalocomplex H 20 ml of triethanolamine and 10 ml of pentanol are introduced into a flat bottom container. During heating and mixing to 50-55° C., slowly 12 g CuCl is added. As a result, a dark-green dense liquid is formed. Before testing the obtained liquid complex H is dissolved in an excessive quantity of pentanol to concentration Cu (II) 1.15%.

Example 4

Purification of Kerosene on Solid Catalyst

A reactor with a magnetic stirrer is utilized, which is formed as a four-neck flat-bottom container with volume of 350 ml, composed OF molybdenum glass and provided with swdlwfmROE, a system of air and oxygen supply and a glass pipe for taking samples A kerosene fraction with a content of mercaptide suffer 80 ppm, a batch of catalyst A (ratio of raw material to catalyst is 62000 ml/g) and Teflon magnetic stirrer were are introduced. The reaction time was four hours. During this time the content of sulfur was reduced to 30 ppm. The samples were taken with interval of 0.5 hour.

Example 5

Purification of Fuel Oil of Gas Condensate on Solid Catalyst

The process was conducted as in Example 2 but instead of kerosene, fuel oil from gas condensate was used, which contained 1200 ppm of mercaptide sulfur (a gas condensate was used which was distilled in interval 56-354° C. with density 0.77 g/cm³ and content of moisture 0.04% mass). The ratio of raw material to catalyst was 7000 ml/g. The temperature of reaction was 120° C. In 1 hour the concentration of sulfur was reduced to 590 ppm.

TABLE 1

Test results of purification of kerosene and gas condensate on solid catalyst.

| Catalyst | Petroleum product to be Purified | Ratio of raw material: Catalytical Solution (ml/Ml) | Temperature ° C. | Content of Mercaptan sulfur, ppm | |
|---|---|---|---|---|---|
| | | | | In Raw Material | After the Reaction |
| A | Kerosene | 120000 | 70 | 80 | 4 hours-20 |
| A | Kerosene | 62000 | 22 | 80 | 10 hours-40 |
| A | Fuel Oil | 7000 | 45 | 1200 | 10 hours-800 |
| B | Kerosene | 62000 | 70 | 80 | 4 hours-25 |
| B | Fuel Oil | 7000 | 120 | 1200 | 2 hours-450 |
| C | Kerosene | 100000 | 70 | 80 | 4 hours-25 |

Example 6

Purification of Fuel Oil from Gas Condensate with the Use of Liquid Catalyst

Liquid complex D is dissolved in an excessive quantity of isobutanol to concentration Cu (II) 1%. Into the reactor described in Example 4, fuel oil was introduced with content of mercaptide sulfur 1200 ppm. The ratio of raw material to solution of catalyst 2000 ml/ml. Temperature of reaction was 100° C. In two hours the concentration of sulfur reduced to 550 ppm.

With increase of concentration of liquid complex in isobutanol to Cu (II) 1.5%, with the same conditions in 2 hours the concentration of sulfur reduced to 450 ppm.

TABLE 2

Test results of purification of kerosene and gas condensate with the use of liquid metalocomplex.

| Catalyst | Petroleum product to be Purified | Ratio of raw material: Catalytical Solution (ml/Ml | Temperature °C. | Content of Mercaptan sulfur, ppm | |
|---|---|---|---|---|---|
| | | | | In Raw Material | After the Reaction |
| D | Kerosene | 100000 | 70 | 80 | 3 hours-20 |
| E | Kerosene | 100000 | 22 | 80 | 3 hours-40 |
| E | Fuel Oil | 7000 | 120 | 1200 | 4 hours-300 |
| F | Fuel Oil | 7000 | 70 | 1200 | 4 hours-800 |
| F | Fuel Oil | 4000 | 120 | 1200 | 2 hours-200 |
| G | Fuel Oil | 7000 | 70 | 1200 | 4 hours-750 |
| H | Fuel Oil | 7000 | 120 | 1200 | 4 hours-720 |
| D | Raw Oil ** | 4000 | 70 | 2300 | 4 hours-1600 |
| F | Raw Oil | 4000 | 22 | 2300 | 4 hours-1950 |

*Catalytic solution contains 1% $Cu^{2+}$
**Oil with density of $0.80 g/cm^3$ with the output fraction 28-360° C. 88%, content of paraffin hydrocarbon 65%, naphten-26% was used.

Examples 7-8 show that it is not possible to keep the objects of the present invention if parameters of catalyst deviate from the parameters in accordance with the present invention.

Example 7

Synthesis of the complex is performed as in Example 1 but instead acetonitryl, chloroform is utilized. During with the process of purification of kerosene in accordance with FIG. 2, the content of mercaptan sulfur is reduced to 60 ppm.

Example 8

Synthesis of the complex is performed as in Example 1, but the reaction solution is not heated. When the purification is performed with Example 2, the content of mercaptide sulfur is reduced to 40 ppm.

It will be understood that each of the elements described above, or two or more together, may also find a useful application in other types of substances and methods differing from the type described above.

While the invention has been illustrated and described as embodied in catalyst and method for alkali-free purification of oil raw material from mercaptans, it is not intended to be limited to the details shown, since various modifications and structural changes may be made without departing in any way from the spirit of the present invention.

Without further analysis, the foregoing will so fully reveal the gist of the present invention that others can, be applying current knowledge, readily adapt it for various applications without omitting features that, from the standpoint of prior art, fairly constitute essential characteristics of the generic or specific aspects of this invention.

The invention claimed is:

1. A catalyst for alkali-free purification of oil raw materials, consisting of a metalocomplex selected from the group consisting of a solid metalocomplex and a liquid metalocomplex, the solid metalocomplex and liquid metalocomplex having a general formula $(Cu''Cl)_2O(L_1)_{2-4}(L_2)_{1-4}$, where $L_1$ is amino alcohol, $L_2$ is acetonitryl or single atom alcohol.

2. A catalyst for alkali-free purification of oil raw materials, consisting of a metalocomplex selected from the group consisting of a solid metalocomplex and a liquid metalocomplex with a general formula $(Cu'Cl)_2O(L_1)_{2-4}(L_2)_{1-4}$, where Li is amino alcohol, $L_2$ is acetonitryl or single atom alcohol, wherein as the aminoalcohol a compound of a general formula $N(R_1)(R_2)(R_3)(OH)_{1-3}$ is utilized, where $R_1=C_2H_4$, $R_2=H, C_2H_4, C_2H_5, R_3=H, C_2H_4, CnH_{2n+1}$, where n=2-17.

3. A catalyst for alkali-free purification of oil raw materials, consisting of a metalocomplex selected from the group consisting of a solid metalocomplex and a liquid metalocomplex with a general formula $(Cu'Cl)_2O(L_1)_{2-4}(L_2)_{1-4}$, where Li is amino alcohol, $L_2$ is acetonitryl or single atom alcohol, wherein as the single atom alcohol a substance selected from the group consisting of isopropanol, butanol, isobutanol and pentanol is utilized.

* * * * *